(12) United States Patent
Schouwink et al.

(10) Patent No.: US 11,363,942 B2
(45) Date of Patent: Jun. 21, 2022

(54) ANGLE-SELECTIVE OPTICAL SYSTEM, STEREO VIDEO ENDOSCOPE HAVING SUCH A SYSTEM, AND METHOD FOR MANUFACTURING SAME

(71) Applicant: OLYMPUS WINTER & IBE GMBH, Hamburg (DE)

(72) Inventors: Peter Schouwink, Ahrensburg (DE); Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 761 days.

(21) Appl. No.: 16/362,039

(22) Filed: Mar. 22, 2019

(65) Prior Publication Data

US 2019/0216302 A1 Jul. 18, 2019

Related U.S. Application Data

(63) Continuation of application No. PCT/EP2017/074074, filed on Sep. 22, 2017.

(30) Foreign Application Priority Data

Oct. 4, 2016 (DE) ...................... 10 2016 219 217.5

(51) Int. Cl.
  *G02B 23/24* (2006.01)
  *A61B 1/00* (2006.01)
  *G02B 27/00* (2006.01)

(52) U.S. Cl.
  CPC ........ *A61B 1/00193* (2013.01); *A61B 1/0011* (2013.01); *A61B 1/00096* (2013.01);
  (Continued)

(58) Field of Classification Search
  CPC ............ A61B 1/00193; A61B 1/00096; A61B 1/0011; A61B 1/00197; G02B 23/2415; G02B 23/243; G02B 27/0018
  See application file for complete search history.

(56) References Cited

U.S. PATENT DOCUMENTS 7,405,877 B1 *  7/2008  Schechterman ... A61B 1/00096
                                                          359/464
7,821,720 B2  10/2010  Wang et al.
(Continued)

FOREIGN PATENT DOCUMENTS

CN  101907763 A  12/2010
CN  103424803 A  12/2013
(Continued)

OTHER PUBLICATIONS

International Search Report dated Nov. 29, 2017 received in PCT/EP2017/074074.

(Continued)

*Primary Examiner* — Howard D Brown, Jr.
(74) *Attorney, Agent, or Firm* — Scully, Scott, Murphy & Presser, P.C.

(57) ABSTRACT

An optical system for use with a stereo video endoscope with a fixed lateral viewing direction. The optical system including: a laterally-viewing distal optical assembly; and a proximal optical assembly, the distal optical assembly and proximal optical assembly jointly establishing a beam path, the proximal optical assembly including: a left channel lens system; and a right channel lens system similarly configured to the left channel lens system; wherein the distal optical assembly establishes an optical axis and is configured to couple incident light along the beam path from an object space into the left channel lens system and into the right channel lens system of the proximal optical assembly; and the optical system comprises an angle-selective optical element with a surface oriented perpendicular to the optical axis of the distal optical assembly, the surface being located in the beam path and coated with an incidence-angle-selective dielectric coating.

10 Claims, 2 Drawing Sheets

(52) U.S. Cl.
CPC ........ *A61B 1/00197* (2013.01); *G02B 23/243* (2013.01); *G02B 23/2415* (2013.01); *G02B 27/0018* (2013.01)

(56) References Cited

U.S. PATENT DOCUMENTS

| | | | | |
|---|---|---|---|---|
| 10,499,794 | B2* | 12/2019 | Gilreath | A61B 1/00091 |
| 10,698,194 | B2* | 6/2020 | Zhao | A61B 1/002 |
| 10,835,102 | B2* | 11/2020 | Ganapati | A61B 1/0638 |
| 2008/0228035 | A1* | 9/2008 | Hagihara | A61B 1/127 |
| | | | | 600/176 |
| 2009/0290236 | A1* | 11/2009 | Wang | G02B 23/243 |
| | | | | 359/753 |
| 2010/0309555 | A1* | 12/2010 | Southwell | G02B 5/281 |
| | | | | 359/586 |
| 2013/0176638 | A1* | 7/2013 | Schouwink | G02B 5/04 |
| | | | | 359/834 |

FOREIGN PATENT DOCUMENTS

| | | |
|---|---|---|
| DE | 10 2010 027 079 A1 | 1/2012 |
| DE | 10 2010 036 285 A1 | 3/2012 |
| DE | 10 2014 206 513 A1 | 10/2015 |
| JP | 2001-281409 A | 10/2001 |
| JP | 2005-208519 A | 8/2005 |
| WO | 2008/003603 A2 | 1/2008 |
| WO | 2016/012248 A1 | 1/2016 |

OTHER PUBLICATIONS

Chinese Office Action dated Nov. 3, 2020 in Chinese Patent Application No. 201780054032.1.

* cited by examiner

ANGLE-SELECTIVE OPTICAL SYSTEM, STEREO VIDEO ENDOSCOPE HAVING SUCH A SYSTEM, AND METHOD FOR MANUFACTURING SAME

CROSS-REFERENCE TO RELATED APPLICATION

The present application is a continuation of PCT/EP2017/074074 filed on Sep. 22, 2017, which is based upon and claims the benefit to DE 10 2016 219 217.5 filed on Oct. 4, 2016, the entire contents of each of which are incorporated herein by reference.

BACKGROUND

Field

The present disclosure relates to an optical system of a stereo video endoscope, and in particular, to an optical system of a stereo video endoscope with a fixed lateral viewing direction comprising a laterally-viewing distal optical assembly and a proximal optical assembly that jointly establish a beam path, wherein the proximal optical assembly comprises a left channel lens system and a right channel lens system that are similarly configured, and wherein the distal optical assembly establishes an optical axis and is configured to couple incident light along the beam path from an object space into the left channel lens system and into the right channel lens system of the proximal optical assembly.

Moreover, the present disclosure relates to a stereo video endoscope with a fixed lateral viewing direction, as well as a method to manufacture an optical system of a stereo video endoscope with a fixed lateral viewing direction, wherein the optical system comprises a laterally-viewing distal optical assembly and a proximal optical assembly that jointly establish a beam path, wherein the proximal optical assembly comprises a left channel lens system and a right channel lens system that are similarly configured, and wherein the distal optical assembly establishes an optical axis and is configured to couple incident light along the beam path from an object space into the left channel lens system and into the right channel lens system of the proximal optical assembly.

Prior Art

Video endoscopes, in which the light entering at a distal tip of an endoscope shaft is directed through an optical system onto one or more images sensors, are known in different designs. There are endoscopes with a direct view, a so-called 0° viewing direction, endoscopes with a (fixed) lateral viewing direction as well as endoscopes with an adjustable viewing direction (also called V-DOV endoscopes).

Moreover, stereo video endoscopes are known which are designed to record a stereoscopic image pair and/or two stereoscopic video channels. With such instruments, it is possible to create a 3D image of an object in an examination or operating room lying distally in front of the end of the endoscope shaft.

Stereo video endoscopes with a lateral viewing direction are laterally-viewing endoscopes with a fixed viewing direction that deviates from the direct view. Such endoscopes frequently comprise a prism arrangement consisting of a plurality of prisms that reflect the light beams twice which enter the optical system from the object space at an angle to the longitudinal axis of the endoscope shaft and on the correct side in the direction of the endoscope shaft. Such an endoscope is for example known from DE 10 2014 206 513 A1 by Olympus Winter & Ibe, Hamburg.

A deflection prism arrangement of such a stereo video endoscope typically comprises two or three prisms. The prisms are repeatedly cemented to each other at their common boundary surfaces. In such a deflection prism arrangement, the reflection of the incident light bundle occurs at two reflecting boundary surfaces of a second prism that are angled relative both to the optical axis of the entrance lens as well as to the longitudinal axis of the endoscope shaft. The second prism of the deflection prism arrangement is located, in the direction of incident light, behind a first prism that is arranged directly behind the entrance lens. The angled reflecting boundary surface of the second prism at which the second reflection occurs partially forms a common boundary surface with the first prism through which the incident light beams first pass.

The entrance lens of the optical system of such a stereo video endoscope defines the optical axis of the optical system. The optical system comprises diaphragms or meniscuses that establish a field of view of the optical system. Light bundles that enter the optical system from within the field of view are imaged by the optical system on one or more image sensors. Light bundles that enter the optical system from outside of the field of view frequently cause reflections within the optical system and generate so-called "ghost images" or "flares".

A known deflection prism group in which such ghost images can arise comprises a first prism and a second prism that are cemented to each other. The first prism has an entrance side and an exit side, wherein the entrance side is angled relative to the exit side. The exit side of the first prism directly borders the second entrance side of the second prism. For example, the first and the second prism are cemented to each other at these two sides. The second prism furthermore comprises a reflection side and a second exit side. Light that enters the deflection prism group outside of the field of view passes through the entrance side of the first prism and exits its exit side. The light then passes directly through the second entrance side into the second prism, is reflected on the reflection side within the second prism and leaves it at the exit side.

A peripheral light beam entering the optical system at a large angle relative to the optical axis of the entrance lens passes through the entrance lens into the prism and passes through its first entrance side and exit side. The light beam also passes through the second entrance side of the second prism at the same time as the first exit side. As already mentioned, these two prism surfaces can be cemented to each other. The light beam is then reflected by the reflection side of the second prism and contacts the common boundary surface between the first and second prism at a sharp angle, i.e., contacts the second entrance side of the second prism from the rear side. There, the light beam undergoes Fresnel reflection or total reflection and is reflected back to the reflection side of the second prism. From there, it again passes to the second entrance side of the second prism and is again reflected e.g. with total reflection by this boundary surface from the inside. Then the light beam passes into a left or right channel lens system where it generates a ghost image. This quadruple reflection in the deflection prism group which is known per se is undesirable.

SUMMARY

It is therefore an object to provide an optical system of a stereo video endoscope with a fixed, lateral viewing direction, a stereo video endoscope with a fixed, lateral viewing direction, as well as a method for manufacturing an optical system of a stereo video endoscope with a fixed, lateral viewing direction that is less sensitive to incident light bundles from the outside of the field of view.

Such object can be achieved by an optical system of a stereo video endoscope with a fixed lateral viewing direction comprising a laterally-viewing distal optical assembly and a proximal optical assembly that jointly establish a beam path, wherein the proximal optical assembly comprises a left channel lens system and a right channel lens system that are similarly configured, and wherein the distal optical assembly establishes an optical axis and is configured to couple incident light along the beam path from an object space into the left channel lens system and into the right channel lens system of the proximal optical assembly, wherein the optical system comprises an angle-selective optical element with a surface oriented perpendicular to the optical axis of the distal optical assembly, wherein this surface located in the beam path is coated with an incidence-angle-selective dielectric coating.

Light bundles entering the optical system that enter the optical system from a field of view in the object space pass through the first entrance side of the first prism, are reflected at the boundary surface of the prism body and pass through the first exit side of the first prism. The first exit side of the first prism can be cemented to the second entrance side of the second prism. The light bundles pass through this boundary surface to the second entrance side of the second prism. They are deflected at the boundary surface of the prism body and pass to the rear reflection side of the second prism. From there, the light bundles are reflected back to the second entrance side of the second prism and undergo total reflection in the prism body within the prism body of the second prism at this boundary surface. The light bundles are hence reflected at an inner side of the second entrance side. From there, the light bundles leave the deflection prism group through the exit side of the second prism.

In the context of the present description, a "lateral viewing direction" or the term "laterally viewing" is understood as follows: The stereo video endoscope has a shaft. This shaft is rigid or flexible. In the case of a rigid shaft, it has a direction of longitudinal extension. In the case of a flexible shaft, the shaft extends in a direction of longitudinal extension at a distal end region. The viewing direction of the endoscope forms an angle with its direction of longitudinal extension that is different from zero. This angle is constant. For example, such an angle is 30°.

In the provided optical system, a quadruple reflection from the boundary surfaces of the deflection prism group as is known per se from the prior art is advantageously excluded. With stereo video endoscopes, the reflective surface of the second prism must be greater than is the case with prisms of endoscopes that do not provide a stereoscopic image. This is necessary since the greatest possible stereo base should be realized for the right and left stereo channel. A large stereo base makes it possible to create a large 3-D effect. This design requirement leads to the aforementioned danger of multiple reflections, such as the described quadruple reflection. These reflections create undesirable ghost images.

An incidence-angle-selective dielectric coating can ensure that an angle-selective optical system is provided. At least a large majority of the light bundles falling into the optical system from outside of the field of view are reflected by the incidence-angle-selective dielectric coating. In other words, incident light bundles therefore do not enter the optical system at a large angle to the optical axis. They are correspondingly unable to generate image distortions there such as ghost images.

The incidence-angle-selective dielectric coating can be configured such that its angle-selective function that restricts the light bundles transmitted by the coating to such light bundles that enter the optical system at a given angle relative to the optical axis. This given angle can correspond to the opening angle that is established by the field of view of the optical system. Only light bundles that enter the optical system at an angle of incidence less than or equal to this threshold angle (the angle to the optical axis is measured) pass through the incidence-angle-selective dielectric coating.

According to one embodiment, the distal optical assembly can comprise an entrance lens, a deflection prism group and an exit lens sequentially in the direction of incident light, wherein the deflection prism group comprises a first prism and a second prism sequentially in the direction of incident light, wherein the first prism comprises a first entrance side and a first exit side oblique thereto, and wherein the second prism comprises a second entrance side, a reflection side and a second exit side, wherein the surface located in the beam path is the first entrance side of the first prism, and this first entrance side is coated with the incidence-angle-selective dielectric coating.

According to another embodiment, the optical system can comprise an entrance window, and the incident light from the object space passes through this entrance window into the distal optical assembly, wherein the surface located in the beam path is one side of the entrance window, and this side is coated with the incidence-angle-selective dielectric coating.

In this context, an inner side of the entrance window facing the distal optical assembly can be coated with the incidence-angle-selective dielectric coating.

Where the coating of the first entrance side of the first prism and/or the inner side of the entrance window is provided, the angle-dependent selection of the incident light bundles occurs directly at the entrance of the optical system. In other words, light bundles entering the optical system from an exterior space only reach one of these boundary surfaces that lie very far to the front in the direction of incidence in order to minimize the interference arising within the optical system.

According to another embodiment, the incidence-angle-selective dielectric coating can be a multilayer that is composed of at least one double layer of two thin layers with different refractive indexes.

In this case, the multilayer can comprise a plurality of periodically sequential double layers like a Bragg mirror.

According to another embodiment, i the optical system can be configured to receive monochromatic light, for example to generate black/white or grayscale images. To accomplish this, a corresponding filter can be provided before the optical system. The left and/or the right channel lens system can also comprise image sensors that perform a conversion of the received light signals into a grayscale image signal. Likewise, narrow-band filters, or those that are approximately transparent to one wavelength can be provided for the image sensors.

Dielectric coatings can cause precisely defined optical interference between the reflected, or respectively transmitted partial beams of an incident light bundle. In order to exploit this effect, the incident light bundle can be divided almost arbitrarily into transmission and reflection, i.e., into a transmitted and a reflected light bundle.

The incident light bundle occurs both at the surface of the dielectric layer as well as at boundary surface between the dielectric layer and the substrate (which can be the material of the coated optical element). A reflected partial beam always arises. These two reflected partial beams manifest a phase shift relative to each other. It corresponds to the product of the refraction index and geometric thickness of the layer. In this case, the phase jump upon being reflected at the more optically dense medium should not be left unconsidered. The geometric thickness of the layer depends on the angle of incidence of the incident light bundle. If the light bundle enters at a greater angle to the optical axis, the geometric thickness is greater than if it entered nearly parallel to the optical axis.

This geometrically-related difference in the path length causes the phase difference between the first partial beam reflected at the top side of the dielectric coating and the second partial beam reflected at the boundary layer to the substrate to depend on the angle of incidence of the beam bundle. This yields angle-dependent change in the phase difference. This angle length dependency causes angle-dependent interference phenomena between the two partial beams; in other words, an angle-dependent reflectivity of the dielectric layer.

When the geometric layer thickness is correctly selected and given the selection of the appropriate material, the incidence-angle-selective dielectric coating that can be provided in this manner ensures that incident light bundles from outside of the field of view are reflected at the dialectic coating and thus do not enter into the optical system. In this context, the combination of the layer thickness and refraction index of the employed dielectric material must always be taken into account.

Similar to a Bragg mirror, the angle-dependent reflectivity is sharper when a double layer of two thin layers with different refraction indexes is used instead of one dielectric layer. This effect is further enhanced when instead of one double layer, a plurality of double layers is used in a multilayer. The more layers such a multilayer comprises, or respectively the more double layers such a multilayer comprises, the sharper its selectivity with respect to the angle of incidence.

According to another embodiment, the incidence-angle-selective dielectric coating can comprise a plurality of microprisms.

A coating consisting of microprisms can be obtainable by photolithographic methods. For this purpose, an applied dielectric layer is subsequently structured. It is also possible to use printing or stamping methods to manufacture the microprisms by means of which a corresponding structure of the surface of the dielectric coating can be achieved.

Such object can also be achieved by a stereo video endoscope with a fixed, lateral viewing direction that comprises an optical system according to one or more of the aforementioned embodiments. The same or similar advantages apply to the stereo video endoscope as were previously mentioned with respect to the optical system itself so that repetitions will therefore be omitted.

Such object can be further achieved by a method to manufacture an optical system of a stereo video endoscope with a fixed lateral viewing direction, wherein the optical system comprises a laterally-viewing distal optical assembly and a proximal optical assembly that jointly establish a beam path, wherein the proximal optical assembly comprises a left channel lens system and a right channel lens system that are similarly configured, and wherein the distal optical assembly establishes an optical axis and is configured to couple incident light along the beam path from an object space into the left channel lens system and into the right channel lens system of the proximal optical assembly, wherein the method comprises providing the optical system with an angle-selective optical element that comprises a surface oriented perpendicular to the optical axis of the distal optical assembly, wherein this surface located in the beam path is coated with an incidence-angle-selective dielectric coating.

The same or similar advantages apply to the method for manufacturing an optical system of a stereo video endoscope with a fixed lateral viewing direction as were previously mentioned with respect to the optical system itself.

The method can further comprises applying a multilayer as an incidence-angle-selective dielectric coating consisting of at least one double layer of two thin layers with different refraction indexes.

Furthermore, a plurality of periodically sequential double layers can be applied as a multilayer like a Bragg mirror.

An angle-selective dielectric coating can furthermore be provided with a plurality of microprisms manufactured on the surface as an incidence-angle-selective dielectric coating.

Further features will become apparent from the description of the embodiments together with the claims and the attached drawings. Embodiments can fulfill individual features or a combination of several features.

BRIEF DESCRIPTION OF THE DRAWINGS

The embodiments are described below, without restricting the general idea of the invention, using exemplary embodiments with reference to the drawings, wherein express reference is made to the drawings with regard to all details that are not explained in greater detail in the text. In the following.

In the drawings, in each case the same or similar elements and/or parts are provided with the same reference numbers, so that in each case a repeated introduction is omitted.

DETAILED DESCRIPTION

Figure 1:
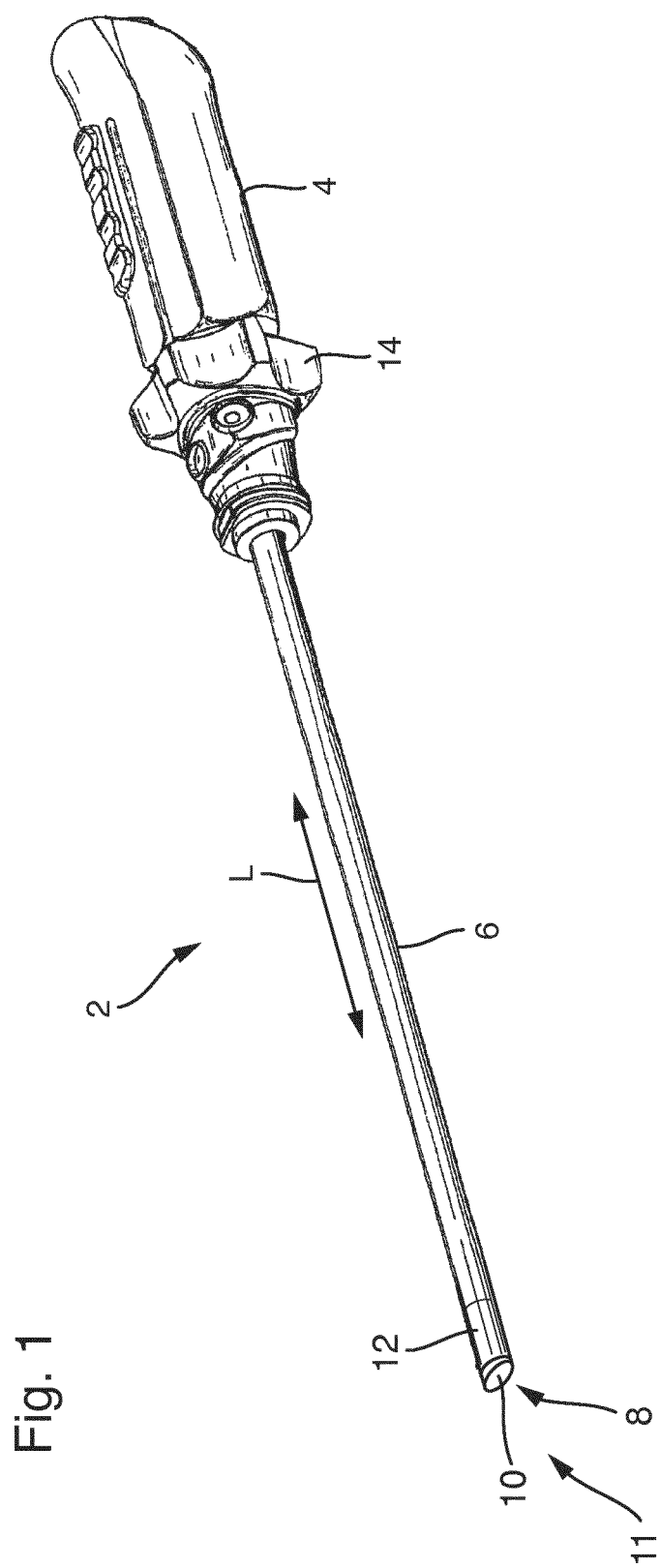
FIG. 1 illustrates a stereo video endoscope in a schematically simplified representation.

FIG. 1 shows a schematically simplified perspective representation of a stereo video endoscope 2 comprising a proximal handle 4 to which a rigid endoscope shaft 6 can be connected. The endoscope shaft 6, also known as an insertion portion, can be both flexible or semi-flexible. An entrance window 10 through which light from an object space 11, such as from a surgical and/or observation field enters an optical system (not shown in FIG. 1) of the stereo video endoscope 2, is located on a distal tip 8 of the endoscope shaft 6. The optical system of the stereo video endoscope 2 can be arranged in a distal section 12 of the endoscope shaft 6. The optical system images objects that are located in the object space 11 on image sensors. These image sensors can be those with a high resolution such as HD, 4K or the following technologies.

The shown stereo video endoscope 2 is a surgical instrument. In addition, the endoscope has a fixed, lateral viewing direction. The entrance window 10 is mounted at an angle in the endoscope shaft 6 so that an optical axis of the entrance lens of the optical system (not shown) encloses a fixed angle with a direction of longitudinal extension L of the endoscope shaft 6 of the stereo video endoscope 2. This angle can be between 10° and 30°.

A change in the viewing direction about a longitudinal axis of the endoscope shaft 6 is effectuated by a rotation of the handle 4. The optical system in the distal section 12 also rotates during this rotation of the handle 4. To retain the horizontal position of the displayed image, a rotary wheel 14 is held while rotating the handle 4. As a result, the image sensors in the inside of the endoscope shaft 6 do not also perform the rotational movement.

Figure 2:
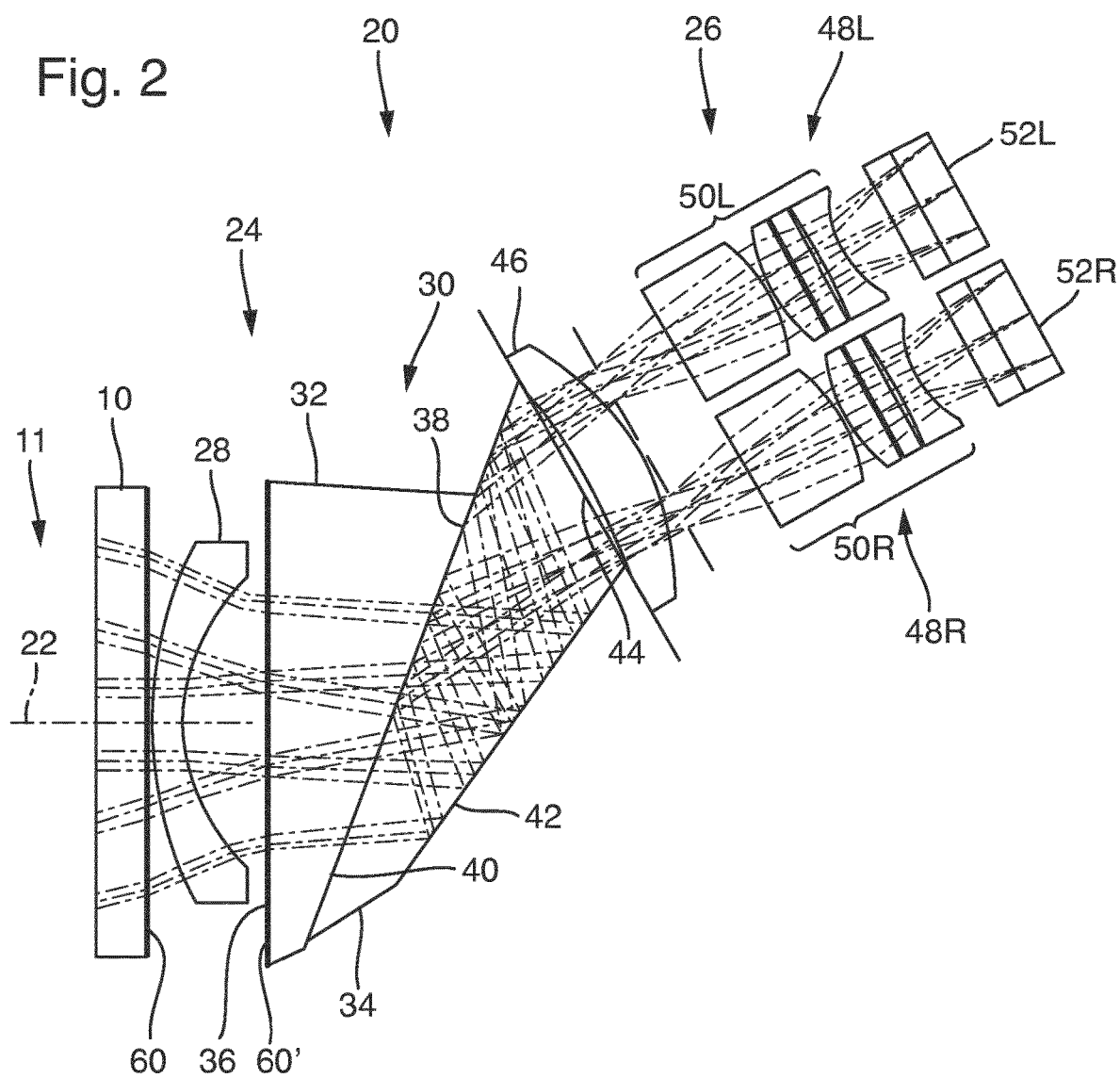
FIG. 2 illustrates a schematically simplified representation of an optical system of such a stereo video endoscope.

FIG. 2 shows in a schematically simplified representation an optical system 20 that can be used in the stereo video endoscope 2, such as that shown in FIG. 1.

The optical system 20 defines the fixed, lateral viewing direction of the stereo video endoscope 2. The optical axis 22 encloses a fixed angle, such as 30° with the direction of longitudinal extension L of the endoscope shaft 6. The optical system 20 comprises a laterally-viewing distal optical assembly 24 and a proximal optical assembly 26. Light entering through the entrance window 10 from the object space 11 first contacts the entrance lens 28 and then enters a deflection prism group 30 of the distal optical assembly 24. The deflection prism group 30 sequentially comprises a first prism 32 and a second prism 34 in the direction of incident light.

In the direction of incident light, the light bundles that leave the entrance lens 28 first pass through a first entrance side 36 of the first prism 32. The light bundles pass through the body of the first prism 32 and reach its first exit side 38. The first exit side 38 is at an angle relative to the first entrance side 36. The first prism 32 and the second prism 34 can be cemented to each other. The second prism 34 comprises a second entrance side 40 through which the light exiting the first prism 32 through its first exit side 38 enters the second prism 34. The first exit side 38 of the first prism 32 and the second entrance side 40 of the second prism 34 can be to each other in the portrayed embodiment. The second prism 34 furthermore comprises a reflection side 42 that is at an angle relative to the second entrance side 40. The light bundles entering the second prism 34 through the second entrance side 40 are reflected by the reflection side 42 of the second prism 34. From there, they contact the second entrance side 40 of the second prism 34 from the rear side. The light bundles are reflected there at an angle such that they then leave the second prism 34 at its second exit side 44. From there, the light bundles continue in the direction of incident light to reach an exit lens 46 of the distal optical assembly 24.

The proximal optical assembly 26 comprises a left channel lens system 48L and a right channel lens system 48R. The left and the right channel lens systems 48L, 48R are constructed similarly or identically. They are furthermore arranged such that a left optical axis (not shown in FIG. 2) and a right optical axis of the left, or respectively right channel lens system 48L, 48R are aligned parallel to each other. The left channel lens system 48L comprises an imaging left lens group 50L that images the incident light on a left image sensor 52L. Correspondingly, the right channel lens system 48R comprises an imaging right lens group 50R that images the incident light on a right image sensor 52R.

The distal optical assembly 24 is configured to couple incident light bundles from the object space 11 both into the left channel lens system 48L as well as into the right channel lens system 48R.

The entire surface of the reflective side 42 of the second prism 34 can be provided with a reflective coating. The reflective coating can be aluminum (Al) or silver (Ag) and can be vapor-deposited onto the outside of the second prism 34 on the reflection side 42.

The surface of the reflection side 42 of the second prism 34 is substantially larger with stereo video endoscopes than with endoscopes that do not provide stereoscopic images. This is necessary in order to enable a very large spacing of the left and right stereo channel. Such a large stereo base enables a strong 3-D effect.

Such a prism construction is however associated with the technical disadvantage that multiple reflections quickly arise which generate a so-called ghost image. Such ghost images are generated by peripheral light beams that enter the optical system 20 from the object space 11 at a wide angle relative to the optical axis 22.

Such a peripheral light beam passes through the entrance lens 28 into the first prism 32 and from there into the second prism 34. It contacts the reflection side 42 of the second prism 34, is reflected there, and contacts the boundary surface at a sharp angle between the first and the second prism 32, 34. From there, it is reflected back to the reflection side 42 of the second prism 34 and again reaches the second entrance side 38 of the second prism 34.

Total reflection again occurs at this boundary surface so that the light beam then leaves the deflection prism assembly 30 through the exit side 44 and generates a ghost image in the left or right channel lens system 48L, 48R.

In order to suppress such peripheral light beams, the optical system 20 comprises an angle-selective optical element that comprises a surface located in the beam path which is oriented perpendicular to the optical axis 22 of the distal optical assembly 24. This surface is provided with an incidence-angle-selective dielectric coating.

According to an exemplary embodiment, such an incidence-angle-selective dielectric coating 60 can be provided on an inner side of the entrance window 10 facing the distal optical assembly 24. Alternatively or in addition, such a dielectric coating 60' can be provided on the first entrance side 36 of the first prism 32.

The incidence-angle-selective dielectric coating 60, 60' ensures that peripheral light beams that enter the optical system 20 from the outside of the field of view are reflected back by the coating into the object space 11. Such peripheral light beams do not enter any further into the optical system 20 and are correspondingly also incapable of causing image flaws there.

Figure 3:
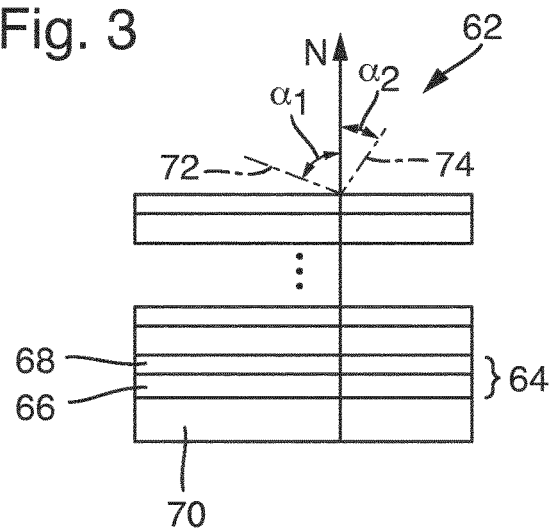
FIG. 3 illustrates a schematic and simplified representation of a multilayer in a cross-section.

The incidence-angle-selective dielectric coating 60, 60' can be a multilayer as represented schematically and simplified in a cross-section in FIG. 3.

The incidence-angle-selective dielectric coating 60 in the portrayed exemplary embodiment is a multilayer 62 that is composed of a plurality of double layers 64. Each double layer 64 consists of a first layer 66 with a first refractive index n1 and of a second layer 68 with a second refractive index n2. The multilayer 62 can be applied to the material of the entry window 10 or the first prism 32 that is schematically portrayed in FIG. 3 as a substrate 70. In addition to their refractive index n1, n2, the individual layers 66, 68 are also distinguished by their layer thickness d1, d2 that is measured in the direction of the surface normal N of the substrate 70 and can lie between at least ten nanometers (nm) and a few micrometers (µm). The surface normal N at least approximately corresponds to the direction of the optical axis 22.

Part of an incident light bundle is reflected at each of the boundary surfaces between the first and second layer 66, 68 and also at the surface of the multilayer 62, as well as the boundary surface of the substrate 70. The reflected partial beams that arise in this manner manifest an incidence-angle-dependent phase shift relative to each other that is determined by the refractive index n1, n2 and the path traveled in the respective material.

This path depends on the layer thickness d1, d2 of the individual layers, and also on the angle of incidence, i.e., an angle relative to the surface normal N. This yields an angle dependence of the reflectivity (and hence the transmission as well) of the multilayer 62. Accordingly, the phase shift for an e.g. first light beam 72 entering at a large angle α1 to the surface normal N is greater than for a second light beam 74 that contacts the multilayer 62 at a small angle of incidence α2 relative to the surface normal N.

By correspondingly selecting material for the first and second layer 66, 68 relative to the refractive index n1, n2 and their layer thickness d1, d2, the reflection, or respectively transmission properties of the multilayer 62 can be adjusted so that only light beams from within the viewing angle of the optical system 20 pass through the incidence-angle-selective dielectric coating 60, 60'. The number of double layers 64 in the multilayer 62 determines the sharpness of the angle dependence as is the case with a Bragg mirror.

In the method to manufacture an optical system 20 of a stereo video endoscope 2 with a fixed lateral viewing direction, the angle-selective optical element is added to the optical system 20 such as the entrance window 10, or the first prism 32. This angle-selective optical element comprises a surface that is located in the beam path of the optical system 20, and encloses an at least approximately perpendicular angle with the optical axis 22 of the optical system 20. This surface is provided with an incidence-angle-selective dielectric coating 60, 60'. In addition to a multilayer 60 portrayed in FIG. 3, the same can be replaced with an arrangement with a plurality of microprisms.

It is furthermore provided that the procedure is similar in a method for repairing a stereo video endoscope 2 with a fixed lateral viewing direction. The deflection prism group 30 of a conventional optical system 20 can be replaced with a deflection prism group 30 that comprises an angle-dependent dielectric coating 60'. It is also provided that the entrance window 10 can be replaced with an entrance window 10 that comprises an angle-selective dielectric coating 60, such as on its inner side. It is also possible to completely exchange the entire distal optical assembly 24, or even the complete optical system 20.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

2 Stereo video endoscope
4 Handle
6 Endoscope shank
8 Distal tip
10 Entrance window
11 Object space
12 Distal section
14 Rotary wheel
15 Optical system
22 Optical axis
24 Distal optical assembly
26 Proximal optical assembly
28 Entrance lens
30 Deflection prism group
32 First prism
34 Second prism
36 First entrance side
38 First exit side
40 Second entrance side
42 Reflection side
44 Second exit side
46 Exit lens
48L Left channel lens system
48R Right channel lens system
SOL Left lens group
50R Right lens group
52L Left image sensor
52R Right image sensor
60, 60' Dielectric coating
62 multilayer
64 Double layer
66 First layer
68 Second layer
70 Substrate
72 First light beam
74 Second light beam
L Direction of longitudinal extension
N Surface normal

The invention claimed is:

1. An optical system for use with a stereo video endoscope with a fixed lateral viewing direction, the optical system comprising:
    a laterally-viewing distal optical assembly; and
    a proximal optical assembly, the distal optical assembly and proximal optical assembly jointly establishing a beam path, the proximal optical assembly comprising:
        a left channel lens system; and
        a right channel lens system similarly configured to the left channel lens system;
    wherein the distal optical assembly establishes an optical axis and is configured to couple incident light along the beam path from an object space into the left channel lens system and into the right channel lens system of the proximal optical assembly; and
    the optical system further comprises an angle-selective optical element with a surface oriented perpendicular to the optical axis of the distal optical assembly, the surface being located in the beam path and being coated with an incidence-angle-selective dielectric coating.

2. The optical system according to claim 1, wherein the distal optical assembly comprises:
    an entrance lens;
    a deflection prism group; and
    an exit lens, the entrance lens, deflection prism group and exit lens being provided sequentially in a direction of incident light;
    wherein the deflection prism group comprises a first prism and a second prism, provided sequentially in the direction of incident light;
    the first prism comprises a first entrance side and a first exit side oblique to the first entrance side;
    the second prism comprises a second entrance side, a reflection side and a second exit side; and the surface located in the beam path is the first entrance side of the first prism, and the first entrance side is coated with the incidence-angle-selective dielectric coating.

3. The optical system according to claim 1, further comprising an entrance window, the incident light from the object space passing through the entrance window into the distal optical assembly;

wherein the surface located in the beam path is one side of the entrance window, and the one side of the entrance window is coated with the incidence-angle-selective dielectric coating.

4. The optical system according to claim 3, wherein the one side of the entrance window is an inner side of the entrance window facing the distal optical assembly.

5. The optical system according to claim 1, wherein the incidence-angle-selective dielectric coating is a multilayer comprising at least one double layer of two layers with different refractive indexes.

6. The optical system according to claim 5, wherein the multilayer comprises a plurality of periodically sequential double layers.

7. A stereo video endoscope with a fixed, lateral viewing direction, the stereo video endoscope comprising:
an insertion portion; and
the optical system according to claim 1 disposed within the insertion portion.

8. A method of manufacturing an optical system for use with a stereo video endoscope with a fixed lateral viewing direction, wherein the optical system comprises a laterally-viewing distal optical assembly and a proximal optical assembly that jointly establish a beam path, wherein the proximal optical assembly comprises a left channel lens system and a right channel lens system that are similarly configured, and wherein the distal optical assembly establishes an optical axis and is configured to couple incident light along the beam path from an object space into the left channel lens system and into the right channel lens system of the proximal optical assembly, the method comprising:
providing the optical system with an angle-selective optical element that comprises a surface oriented perpendicular to the optical axis of the distal optical assembly;
locating the surface in the beam path; and
coating the surface with an incidence-angle-selective dielectric coating.

9. The method according to claim 8, wherein the coating comprises applying a multilayer as the incidence-angle-selective dielectric coating comprising at least one double layer of two layers with different refraction indexes.

10. The method according to claim 9, wherein the coating comprises applying a plurality of periodically sequential double layers as a multilayer.

* * * * *